United States Patent
Haraya et al.

(10) Patent No.: US 10,709,651 B2
(45) Date of Patent: Jul. 14, 2020

(54) COSMETIC COMPOSITION CONTAINING ACYL BASIC AMINO ACID DERIVATIVE AND INORGANIC POWDER

(71) Applicant: AJINOMOTO CO., INC., Tokyo (JP)

(72) Inventors: Nana Haraya, Kawasaki (JP); Shun Kobayashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/631,837

(22) Filed: Jun. 23, 2017

(65) Prior Publication Data

US 2017/0281495 A1   Oct. 5, 2017

Related U.S. Application Data

(63) Continuation of application No. PCT/JP2015/086213, filed on Dec. 25, 2015.

(30) Foreign Application Priority Data

Dec. 25, 2014   (JP) .................. 2014-262160

(51) Int. Cl.
| | |
|---|---|
| A61K 8/42 | (2006.01) |
| A61K 8/44 | (2006.01) |
| A61K 8/19 | (2006.01) |
| A61K 8/27 | (2006.01) |
| A61K 8/29 | (2006.01) |
| A61K 8/26 | (2006.01) |
| A61Q 17/04 | (2006.01) |
| A61Q 15/00 | (2006.01) |
| A61Q 1/06 | (2006.01) |
| A61Q 1/12 | (2006.01) |
| A61K 8/25 | (2006.01) |
| A61K 8/41 | (2006.01) |

(52) U.S. Cl.
CPC .......... *A61K 8/42* (2013.01); *A61K 8/19* (2013.01); *A61K 8/25* (2013.01); *A61K 8/26* (2013.01); *A61K 8/27* (2013.01); *A61K 8/29* (2013.01); *A61K 8/416* (2013.01); *A61K 8/44* (2013.01); *A61Q 1/06* (2013.01); *A61Q 1/12* (2013.01); *A61Q 15/00* (2013.01); *A61Q 17/04* (2013.01); *A61K 2800/622* (2013.01)

(58) Field of Classification Search
None
See application file for complete search history.

(56) References Cited

U.S. PATENT DOCUMENTS

| | | | | |
|---|---|---|---|---|
| 5,582,818 | A * | 12/1996 | Nakanishi ............. | A61K 8/25 424/59 |
| 6,224,888 | B1 * | 5/2001 | Vatter ................... | A61K 8/26 424/401 |
| 2003/0108499 | A1 * | 6/2003 | Smith .................... | A61K 8/044 424/65 |
| 2004/0248812 | A1 | 12/2004 | Hanabusa et al. | |
| 2006/0029626 | A1 | 2/2006 | Yamato et al. | |
| 2006/0120989 | A1 * | 6/2006 | Ricard .................... | A61K 8/37 424/70.31 |
| 2009/0280077 | A1 * | 11/2009 | Yoshida ................. | A61K 8/442 424/59 |
| 2014/0350128 | A1 | 11/2014 | Hanabusa et al. | |

FOREIGN PATENT DOCUMENTS

| | | |
|---|---|---|
| EP | 1 473 027 A1 | 11/2004 |
| JP | 61-7207 A | 1/1986 |
| JP | 2003-300814 A | 10/2003 |
| JP | 2004-323505 A | 11/2004 |
| JP | 2005-2077 A | 1/2005 |
| WO | WO 2013/118896 A1 | 8/2013 |
| WO | WO-2014039437 A2 * | 3/2014 ............. C01B 33/18 |
| WO | WO 2014/142266 A1 | 9/2014 |
| WO | WO 2014/189014 A1 | 11/2014 |

OTHER PUBLICATIONS

Liang et al. Journal of Surfactants and Detergents 2014 17:693-701 available online Dec. 7, 2013 (Year: 2013).*
Kunio Esumi, et al. "Surface Treatment of Inorganic Pigments by $N^e$-Acyllysine," The Chemical Society of Japan, vol. 56, No. 9, 1983, pp. 2569-2571.
Masahiro Suzuki, et al. "$_L$-Lysine based gemini organogelators: their organogelation properties and thermally stable organogels," Org. Biomol Chem, vol. 1, 2003, pp. 4124-4131.
Masahiro Suzuki, et al. "Novel dumbbell-form low-molecular-weight gelators based on $_L$-lysine: their hydrogelation and organogelation properties," New J. Chem. vol. 29, 2005, pp. 1439-1444.

(Continued)

*Primary Examiner* — Robert A Wax
*Assistant Examiner* — Caralynne E Helm
(74) *Attorney, Agent, or Firm* — Oblon, McClelland, Maier & Neustadt, L.L.P.

(57) ABSTRACT

The present invention provides a composition containing component (A): a compound represented by the formula (1)

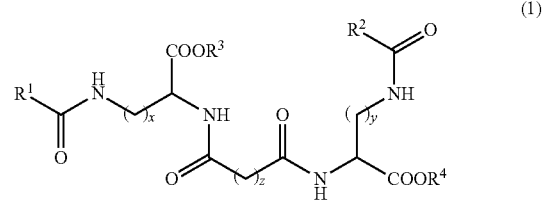

wherein each symbol is as described in the DESCRIPTION, or a salt thereof, and component (B): at least one kind of inorganic powder. The composition can be produced conveniently, shows good dispersibility, and is superior in the sense of use such as moist feeling, feeling of close adhesion and affinity, and a coated film formed from the composition has good condition and is also superior in durability.

5 Claims, No Drawings

(56) References Cited

OTHER PUBLICATIONS

"Manufacturing Technology of Cosmetics Fragrance Journal," 2001, pp. 162-165.
Extended European Search Report dated May 15, 2018 in Patent Application No. 15873264.4, 8 pages.

* cited by examiner

COSMETIC COMPOSITION CONTAINING ACYL BASIC AMINO ACID DERIVATIVE AND INORGANIC POWDER

CROSS REFERENCES TO RELATED APPLICATIONS

This application is a continuation of International Patent Application No. PCT/JP2015/086213, filed on Dec. 25, 2015, and claims priority to Japanese Patent Application No. 2014-262160, filed on Dec. 25, 2014, all of which are incorporated herein by reference in their entireties.

BACKGROUND OF THE INVENTION

Field Of The Invention

The present invention relates to a composition containing (A): an acyl basic amino acid derivative and (B): at least one kind of inorganic powder, which is used for, for example, cosmetics. In addition, it relates to a production method of a surface treatment powder containing (A) and (B).

Discussion Of The Background

Pigments are used for various products such as paint, cosmetics and the like, and are generally often used after coating the surface thereof depending on various objects such as improvement of dispersibility, condition and durability of coated film, color tone and the like and improvement of sense of use and the like. The surface treatment of pigments is very important since it is greatly affected by the production conditions and the like of the product.

As an example of the surface treatment of pigments in cosmetics, in powder foundation, a surface treatment of pigments is performed with a highly polar material by a wet production method or a surface treatment of pigments is performed with a material with a sense of use affording smooth texture, to realize a feeling of non-powdery covering.

As one of the materials used for surface treatment, $N^\varepsilon$-lauroyl-L-lysine is known (non-patent document 1). As characteristics of the surface treatment with $N^\varepsilon$-lauroyl-L-lysine, disclosed are reduced damage on the skin since a lipophilic treatment decreases oil absorption, improvement of attachability, comparatively small coagulation due to compression, enhanced usability and texture and the like (patent document 1, non-patent document 2).

However, the effect of surface treatment with $N^\varepsilon$-lauroyl-L-lysine is not sufficiently satisfactory. In addition, a method of producing a powder surface-treated with $N^\varepsilon$-lauroyl-L-lysine includes dissolving $N^\varepsilon$-lauroyl-L-lysine which is poorly soluble in water in a strong alkaline aqueous solution, and adding the solution dropwise to a hydrochloric acid slurry of pigment to neutralize same, which is followed by filtration, drying, pulverization, and sieve treatment (patent document 1), and the method is very laborious.

It has been reported that a compound represented by the following formula:

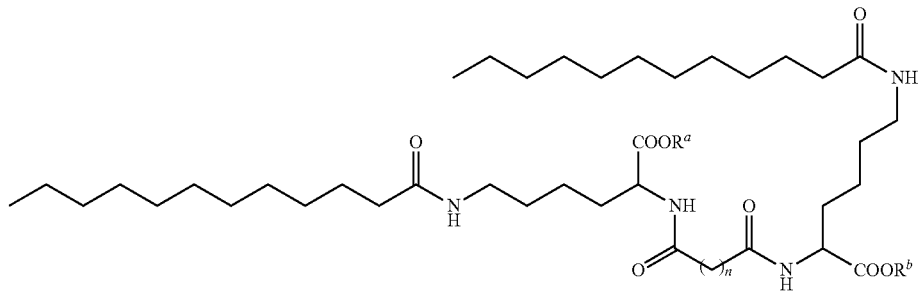

wherein $R^a$ and $R^b$ are each a hydrogen atom or an alkyl group, and n is an integer of 0 to 12, or a salt thereof (hereinafter to be also referred to as "lauroyl amino acid derivative") is useful for gelation or solidifying water and a liquid organic medium (patent document 2, non-patent document 3 and non-patent document 4 etc.).

However, a composition containing a lauroyl amino acid derivative and an inorganic powder, and a cosmetic containing the composition have not been reported heretofore.

DOCUMENT LIST

Patent Documents patent document 1: JP-A-2005-2077
patent document 2: JP-A-2004-323505

Non-Patent Document non-patent document 1: Bull. Chem. Soc. Jpn., 1983, 56, 2569-2571
non-patent document 2: Manufacturing Technology of Cosmetics Fragrance Journal (2001), 162-164
non-patent document 3: Org. Biomol. Chem., 2003, 1, 4124-4131
non-patent document 4: New J. Chem., 2005, 29, 1439-1444

SUMMARY OF THE INVENTION

Problems to be Solved by the Invention

An object of the present invention is to provide a composition which can be produced conveniently, has good dispersibility, is superior in the sense of use such as moist feeling, feeling of close adhesion and affinity, and is superior in the condition and durability of the coated film.

Means of Solving the Problems

The present inventors have conducted intensive studies in an attempt to achieve the above-mentioned object and found that a composition of component (B): at least one kind of inorganic powder coating, which is coated with component (A): a compound represented by the following formula (1) (hereinafter sometimes to be also referred to as "compound (1)") or a salt thereof has good dispersibility, is superior in the sense of use such as moist feeling, feeling of close adhesion, and affinity, and improves the condition and durability of the coated film, which resulted in the completion of the present invention.

Therefore, the present invention provides the following.

[1] A composition comprising component (A): a compound represented by the formula (1)

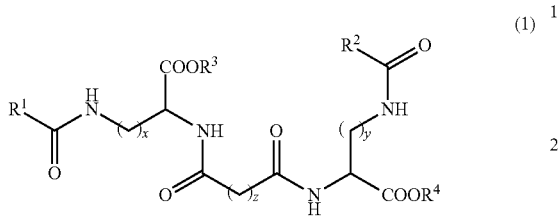

wherein
$R^1$ and $R^2$ are each independently an alkyl group having 5-21 carbon atoms or an alkenyl group having 5-21 carbon atoms,
$R^3$ and $R^4$ are each independently a hydrogen atom, an alkyl group having 1-22 carbon atoms or an alkenyl group having 2-22 carbon atoms,
z is an integer of not less than 0,
x and y are each independently an integer of 2-4, or a salt thereof, and
component (B): at least one kind of inorganic powder.

[2] The composition of [1], wherein component (A) is a compound of the aforementioned formula (1) wherein z is an integer of 0-10, or a salt thereof.

[3] The composition of [1] or [2], wherein component (A) is a compound of the aforementioned formula (1) wherein z is 7 or 8, or a salt thereof.

[4] The composition of any of [1]-[3], wherein component (A) is a compound of the aforementioned formula (1) wherein x and y are each 4, or a salt thereof.

[5] The composition of any of [1]-[4], wherein component (A) is a compound of the aforementioned formula (1) wherein $R^1$ and $R^2$ are each independently a straight-chain alkyl group having 5-15 carbon atoms, or a salt thereof.

[6] The composition of any of [1]-[5], wherein component (A) is a compound of the aforementioned formula (1) wherein $R^3$ and $R^4$ are each a hydrogen atom, or a salt thereof.

[7] The composition of any of [1]-[5], wherein component (A) is a compound of the aforementioned formula (1) wherein $R^1$ and $R^2$ are each independently a straight-chain alkyl group having 5-15 carbon atoms, $R^3$ and $R^4$ are each a hydrogen atom, z is an integer of 0-10, and x and y are each 4, or a salt thereof.

[8] The composition of any of [1]-[5], wherein component (A) is a compound of the aforementioned formula (1) wherein $R^1$ and $R^2$ are each a straight-chain alkyl group having 5-15 carbon atoms, $R^3$ and $R^4$ are each a hydrogen atom, z is 7 or 8, and x and y are each 4, or a salt thereof.

[9] The composition of any of [1]-[8], wherein component (A) is a compound selected from bis($N^\epsilon$-lauroyl-L-lysine) sebacoyl amide, and bis($N^\epsilon$-octanoyl-L-lysine)sebacoyl amide, or a salt thereof.

[10] The composition of any of [1]-[9], wherein component (B) is at least one kind of inorganic powder selected from talc, mica, sericite, iron oxide, titanium oxide, titanium oxide fine particle, zinc oxide, zinc oxide fine particle, silica and aluminum hydroxide.

[11] The composition of any of [1]-[10], wherein weight of component (A)/weight of component (B) is 1/200-1/5.

[12] A cosmetic comprising the composition of any of [1]-[11].

[13] A method of producing a surface-treated powder, comprising coating a surface of component (B): at least one kind of inorganic powder, with component (A): a compound represented by the formula (1)

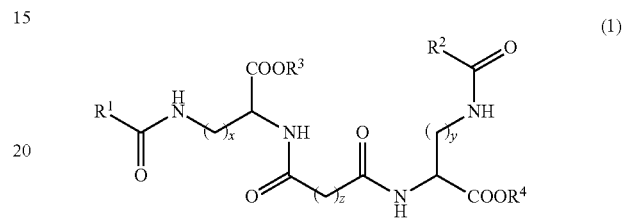

wherein
$R^1$ and $R^2$ are each independently an alkyl group having 5-21 carbon atoms or an alkenyl group having 5-21 carbon atoms,
$R^3$ and $R^4$ are each independently a hydrogen atom, an alkyl group having 1-22 carbon atoms or an alkenyl group having 2-22 carbon atoms,
z is an integer of not less than 0, and
x and y are each independently an integer of 2-4, or a salt thereof.

[14] A surface-treated powder wherein a surface of component (B): at least one kind of inorganic powder is coated with component (A): a compound represented by the formula (1) or a salt thereof.

Effect of the Invention

According to the present invention, a cosmetic composition which can be produced conveniently, has good dispersibility, and is superior in the sense of use such as moist feeling, feeling of close adhesion, and affinity can be provided.

According to the present invention, a cosmetic with less makeup collapse and the like can be provided since a coated film having superior condition and durability can be provided.

DETAILED DESCRIPTION OF THE PREFERRED EMBODIMENTS

The composition of the present invention is characterized in that it is a composition containing component (A): a compound represented by the formula (1)

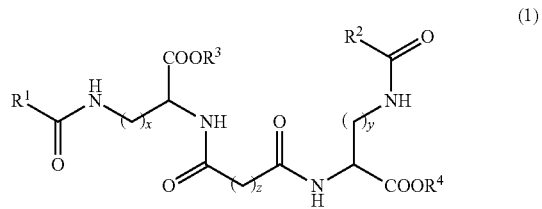

wherein $R^1$ and $R^2$ are each independently an alkyl group having 5-21 carbon atoms or an alkenyl group having 5-21 carbon atoms, $R^3$ and $R^4$ are each independently a hydrogen atom, an alkyl group having 1-22 carbon atoms or an alkenyl group having 2-22 carbon atoms, z is an integer of not less than 0, x and y are each independently an integer of 2-4, or a salt thereof, and component (B): at least one kind of inorganic powder.

The embodiment of the present invention is described in detail in the following.

1. Component (A): a Compound Represented by the Formula (1) (Compound (1)) or a Salt Thereof $R^1$ and $R^2$ are each independently an alkyl group having 5-21 carbon atoms or an alkenyl group having 5-21 carbon atoms.

The alkyl group having 5-21 carbon atoms means a straight-chain or branched-chain alkyl group having 5-21 carbon atoms. Specific examples thereof include pentyl group, isopentyl group, neopentyl group, a hexyl group, isohexyl group, neohexyl group, heptyl group, isoheptyl group, neoheptyl group, octyl group, isooctyl group, nonyl group, isononyl group, decyl group, isodecyl group, undecyl group, dodecyl group, tridecyl group, tetradecyl group, pentadecyl group, hexadecyl group, heptadecyl group, octadecyl group, nonadecyl group, icosyl group and the like.

The alkenyl group having 5-21 carbon atoms means a straight-chain or branched-chain alkenyl group having 5-21 carbon atoms. Specific examples thereof include pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group and the like.

An alkyl group having 5-15 carbon atoms means a straight-chain or branched-chain alkyl group having 5-15 carbon atoms. Specific examples thereof include pentyl group, a hexyl group, heptyl group, octyl group, nonyl group, decyl group, undecyl group, dodecyl group, tridecyl group, tetradecyl group, pentadecyl group and the like.

An alkyl group having 7-11 carbon atoms means a straight-chain or branched-chain alkyl group having 7-11 carbon atoms. Specific examples thereof include heptyl group, octyl group, nonyl group, decyl group, undecyl group and the like.

$R^1$ and $R^2$ are preferably each independently an alkyl group having 5-15 carbon atoms, more preferably each independently an alkyl group having 7-11 carbon atoms.

Preferably, $R^1$ and $R^2$ are each a straight-chain alkyl group. Furthermore, $R^1$ and $R^2$ are preferably the same.

$R^3$ and $R^4$ are each independently a hydrogen atom, an alkyl group having 1-22 carbon atoms or an alkenyl group having 2-22 carbon atoms.

An alkyl group having 1-22 carbon atoms means a straight-chain or branched-chain alkyl group having 1-22 carbon atoms. Specific examples thereof include methyl group, an ethyl group, a propyl group, an isopropyl group, a butyl group, an isobutyl group, a sec-butyl group, a tert-butyl group, a pentyl group, isopentyl group, neopentyl group, a hexyl group, isohexyl group, neohexyl group, heptyl group, isoheptyl group, neoheptyl group, octyl group, isooctyl group, nonyl group, isononyl group, decyl group, isodecyl group, undecyl group, dodecyl group, tridecyl group, tetradecyl group, pentadecyl group, hexadecyl group, heptadecyl group, octadecyl group, nonadecyl group, icosyl group and the like.

An alkenyl group having 2-22 carbon atoms means a straight-chain or branched-chain alkenyl group having 2-22 carbon atoms. Specific examples thereof include ethenyl group, 1-propenyl group, 2-propenyl group, 1-butenyl group, 2-butenyl group, 3-butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group and the like.

Preferably, both $R^3$ and $R^4$ are hydrogen atoms.

z is an integer of not less than 0.

z is preferably an integer of 0-10, more preferably 7 or 8.

x and y are each independently an integer of 2-4.

x and y are each preferably 4.

As a compound represented by the formula (1), the following compounds can be preferably recited.

(Compound A)

A compound wherein $R^1$ and $R^2$ are each independently a straight-chain alkyl group having 5-15 carbon atoms, $R^3$ and $R^4$ are each a hydrogen atom, z is an integer of 0-10, and x and y are each 4.

(Compound B)

A compound wherein $R^1$ and $R^2$ are each a straight-chain alkyl group having 5-15 carbon atoms, $R^3$ and $R^4$ are each a hydrogen atom, z is 7 or 8, and x and y are each 4.

(Compound C)

A compound wherein $R^1$ and $R^2$ are each a straight-chain alkyl group having 7-11 carbon atoms, $R^3$ and $R^4$ are each a hydrogen atom, z is 7 or 8, and x and y are each 4.

Specific examples of the compound represented by the formula (1) include bis($N^\epsilon$-lauroyl-L-lysine)sebacoyl amide, bis($N^\epsilon$-octanoyl-L-lysine)sebacoyl amide, and a salt thereof.

The salt of the compound represented by the formula (1) is not particularly limited. Examples thereof include alkali metal salts such as sodium salt, potassium salt and the like, alkaline earth metal salts such as calcium salt, magnesium salt and the like, inorganic salts such as aluminum salt, salt with zinc and the like, and organic salts such as organic amine salts such as ammonium salt, monoethanolamine salt, diethanolamine salt, triethanolamine salt and the like, basic amino acid salts such as arginine salt, lysine salt and the like, and the like. One kind of these may be used, or two or more kinds selected from the above-mentioned group may be used in a mixture. From the aspects of easy availability, handling property and the like, alkali metal salt, organic amine salt, or basic amino acid salt is preferable, and sodium salt and potassium salt are particularly preferable.

Compound (1) can be produced by a method known per se or a method analogous thereto (JP-A-2004-323505, Org. Biomol. Chem., 2003, 1, 4124-4131, New J. Chem., 2005, 29, 1439-1444 etc.). For example, as shown in the following formula, of compounds (1), symmetrical compound (1') can be produced by reacting $N^\omega$-acyl amino acid (2) and dicarboxylic acid dichloride (3) in an appropriate solvent.

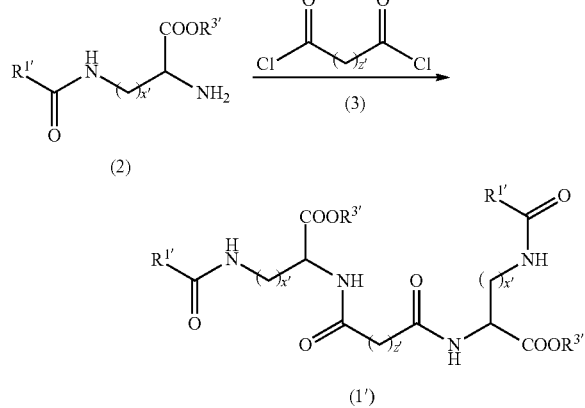

(2) → (1')

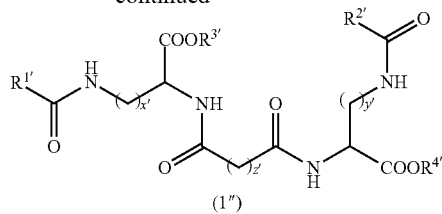

(1'')

wherein $R^{1'}$ is an alkyl group having 5-21 carbon atoms or an alkenyl group having 5-21 carbon atoms, $R^{3'}$ is a hydrogen atom, an alkyl group having 1-22 carbon atoms or an alkenyl group having 2-22 carbon atoms, $z'$ is an integer of not less than 0, and $x'$ is an integer of 2-4.

Examples of the $N^\omega$-acyl amino acid (2) include $N^\varepsilon$-acyl lysine (e.g., $N^\varepsilon$-hexanoyl-L-lysine, $N^\varepsilon$-octanoyl-L-lysine etc.), $N^\delta$-acyl ornithine (e.g., $N^\delta$-hexanoyl-L-ornithine etc.), $N^\gamma$-acyl-$\alpha$, $\gamma$-diaminobutyric acid and the like.

Examples of the dicarboxylic acid dichloride (3) include oxalyl chloride, malonyl chloride, succinyl chloride, glutaryl chloride, adipoyl chloride, pimeloyl chloride, suberoyl chloride, azelaoyl chloride, sebacoyl chloride, dodecanedioyl chloride and the like. The amount of dicarboxylic acid dichloride (3) to be used is generally 0.4-0.6 equivalent relative to $N^\omega$-acyl amino acid (2).

While the solvent is not particularly limited as long as it is inert to the reaction, examples thereof include ethers such as diethyl ether, tetrahydrofuran and the like.

In addition, of compounds (1), asymmetric compound (1'') can be produced as follows. First, $N^\omega$-acyl amino acid (2) and dicarboxylic acid monochloride monoester (4) are reacted in an appropriate solvent to give compound (5) (step 1). Then, the primary ester moiety of the obtained compound (5) is hydrolyzed in the presence of a base such as sodium hydroxide, potassium hydroxide and the like, the carboxylic acid moiety is chlorinated with a chlorinating agent such as thionyl chloride and the like, and the compound is reacted with $N^\omega$-acyl amino acid (2') which is different from $N^\omega$-acyl amino acid (2) used in the aforementioned step 1 (step 2), whereby derivative (1'') can be produced.

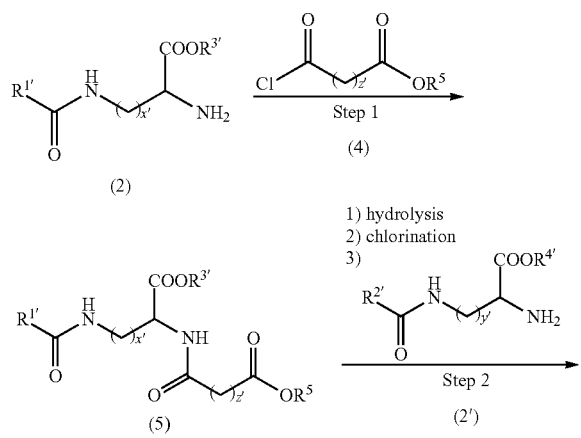

wherein $R^{1'}$, $R^{3'}$, $z'$ and $x'$ are as defined above, $R^{2'}$ is an alkyl group having 5-21 carbon atoms or an alkenyl group having 5-21 carbon atoms, $R^{4'}$ is a hydrogen atom, an alkyl group having 1-22 carbon atoms or an alkenyl group having 2-22 carbon atoms, $R^5$ is an alkyl group such as a methyl group, an ethyl group and the like, and $y'$ is an integer of 2-4.

As $N^\omega$-acyl amino acids (2) and (2'), $N^\omega$-acyl amino acids similar to those mentioned above can be used.

As dicarboxylic acid monochloride monoester (4), a commercially available product can be used as is when it is commercially available, or one produced by a method known per se or a method analogous thereto can also be used.

Compound (1) obtained by the aforementioned method can be converted to a salt of compound (1) by a reaction with alkali metal hydroxide such as sodium hydroxide, potassium hydroxide and the like, alkali earth metal hydroxide such as calcium hydroxide and the like, organic amine base, or the like.

2. Component (B): at Least One Kind of Inorganic Powder

The "inorganic powder" in the present specification is preferably an inorganic powder having a particle size of 0.01 μm-100 μm.

Specific examples of the "inorganic powder" include alumina, talc, kaolin, mica, sericite, bismuth trioxide, bismuth oxychloride, bentonite, smectite, montmorillonite, hectorite, zeolite, calcium carbonate, magnesium carbonate, silicic anhydride, magnesium silicate, aluminum silicate, aluminum silicate magnesium, calcium silicate, barium silicate, strontium silicate, calcium phosphate, magnesium oxide, barium sulfate, magnesium alumina metasilicate, iron oxide(red iron oxide, black iron oxide, yellow iron oxide etc.), chrome oxide, titanium oxide, titanium oxide fine particle, zinc oxide, zinc oxide fine particle, cerium oxide, aluminum oxide, magnesium oxide, chromium hydroxide, ultramarine blue, iron blue, silica, calcium carbonate, magnesium carbonate, calcium phosphate, aluminum hydroxide, barium sulfate, magnesium sulfate, silicon carbide, tungsten acid metal salt, magnesium aluminate, magnesium alumina metasilicate, aluminum chlorohydrate, clay, hydroxyapatite, ceramic powder, boron nitride, aluminum nitride, titanium nitride, silicon nitride, silicone carbide, cobalt titanate, ilmenite, lithium cobalt titanate, cobalt aluminate, inorganic blue pigment, metal powder pigment (e.g., aluminum powder, gold powder, silver powder, iron powder, platinum powder, aluminum powder, copper powder, stainless powder etc.) and the like. Of these, talc, mica, sericite, iron oxide, titanium oxide, titanium oxide fine particle, zinc oxide, zinc oxide fine particle, silica and aluminum hydroxide are preferable, and talc, mica, titanium oxide and silica are more preferable.

In addition, two or more kinds of the above-mentioned inorganic powder may be used in combination. For example, a powder in which aluminum hydroxide is conjugated on the surface of titanium oxide fine particles (titanium oxide ultrafine particle TTO-55(A): manufactured by Ishihara Sangyo Kaisha, LTD.), a powder in which aluminum hydroxide is conjugated on the surface of mica particles or pearl particles (Excel Mica JP-2, Excel Pearl: manufactured by Miyoshi Kasei), a powder in which silica beads are conjugated on the surface of mica particles (SXI-5: manufactured by Miyoshi Kasei), a powder in which titanium oxide and titanium oxide fine particles are conjugated on the surface of mica particles and talc particles (TMC series, TTC series: manufactured by Miyoshi Kasei), a powder in which hydroxyapatite and zinc oxide are conjugated on the surface of sericite particles (Powder La Vie: manufactured by Miyoshi Kasei) and the like can be mentioned. Of these, an inorganic powder conjugated with aluminum hydroxide is preferable.

In the composition of the present invention, the weight ratio of component (A): compound (1) or a salt thereof and component (B): at least one kind of inorganic powder, as weight of component (A)/weight of component (B), is generally 1/1000-1/1, preferably 1/200-1/5, more preferably 1/100-1/10.

The present invention also relates to a cosmetic containing the aforementioned composition of the present invention.

Specific examples of the cosmetic include basic cosmetic (e.g., skin lotion, milky lotion, makeup base, serum, night cream, facial mask, makeup remover product (cleansing gel etc.), nail cream etc.), sun care product (e.g., sunscreen, lotion for sunburn skin etc.), hair treatment agent (e.g., hair treatment, out-bath treatment, serum for hair, split end mender etc.), hair styling products (e.g., brushing lotion, curler lotion, pomado, stick pomade, hair spray for styling, hair mist, hair liquid, styling foam, hair gel, water grease etc.), shaving product (e.g., shaving cream, after-shave lotion etc.), makeup cosmetic (e.g., foundation (solid, cream, liquid etc.), BB cream, CC cream, concealer, rouge, lip gloss, eye shadow, eyeliner, blush, mascara, bronzer etc.), perfumes, lip cream, adiaphoretic, oral cosmetic, tooth paste, bath cosmetic (e.g., bathing powder, bath salt etc.) and the like.

The cosmetic of the present invention may contain components that can be generally added to a cosmetic, as long as the effect of the present invention is not inhibited. Specific examples include amino acids, amino acid derivative, chelating agent, cosmetic powder, lower alcohol, animal and plant extract, nucleic acid, vitamin, enzyme, anti-inflammatory agent, antimicrobial agent, preservative, antioxidant, ultraviolet absorber, adiaphoretic, pigment, dye, oxidation dye, pH adjuster, pearly sheen agent, and wetting agent.

In addition, the present invention relates to a surface-treated powder, characterized in that a surface of component (B): at least one kind of inorganic powder is coated with component (A): a compound represented by the formula (1) or a salt thereof.

In addition, the present invention relates to a production method of a surface-treated powder, characterized in that a surface of component (B): at least one kind of inorganic powder is coated with component (A): a compound represented by the formula (1) or a salt thereof. Examples of the coating treatment method include a method of dispersing component (B) in a liquid of component (A) and the like. Based on a conventionally-used technique, it is possible to further perform drying, pulverization, classification and the like, whereby a surface-treated powder can be produced. The mixing ratio, definitions of (A) and (B) and the like in the production method of the present invention are as defined above.

The composition of the present invention, and a cosmetic containing the composition can be produced according to a conventional method.

Other features of the invention will become apparent in the course of the following descriptions of exemplary embodiments which are given for illustration of the invention and are not intended to be limiting thereof.

EXAMPLES

The present invention is concretely explained in the following by referring to Production Example and Examples. The present invention is not limited by the following Production Example and Examples. Unless particularly indicated, "%" means "wt %".

Production Example 1: Synthesis of bis($N^\varepsilon$-lauroyl-L-lysine)sebacoyl amide disodium salt $N^\varepsilon$-lauroyl-L-lysine (8.2 g, 25 mmol) was dissolved in water (70 g) and 25% aqueous sodium hydroxide solution (10 g), and diethyl ether (80 g) was added. Sebacoyl chloride (3.3 g, 14 mmol) was slowly added to the ether layer. The two-layer solution was stirred for about 1 hr while maintaining at 0° C., and then at room temperature for 23 hr. Then, 75% sulfuric acid was added dropwise to adjust to pH 2, the obtained white precipitate was collected by filtration, washed well with water and dried. The obtained compound was dissolved in an aqueous sodium hydroxide solution to give a 10% aqueous bis($N^\varepsilon$-lauroyl-L-lysine)sebacoyl amide disodium salt solution.

Production Example 2: Synthesis of bis($N^\varepsilon$-octanoyl-L-lysine)sebacoyl amide disodium salt $N^\varepsilon$-octanoyl-L-lysine (6.8 g, 25 mmol) was dissolved in water (70 g) and 25% aqueous sodium hydroxide solution (10 g), and diethyl ether (80 g) was added. Sebacoyl chloride (3.3 g, 14 mmol) was slowly added to the ether layer. The two-layer solution was stirred for about 1 hr while maintaining at 0° C., and then at room temperature for 23 hr. Then, 75% sulfuric acid was added dropwise to adjust to pH 2, the obtained white precipitate was collected by filtration, washed well with water and dried. The obtained compound was dissolved in an aqueous sodium hydroxide solution to give a 10% aqueous bis($N^\varepsilon$-octanoyl-L-lysine)sebacoyl amide disodium salt solution.

$^1$H-NMR of bis($N^\varepsilon$-octanoyl-L-lysine)sebacoyl amide (free form)

$^1$H-NMR (400 MHz, DMSO-$d_6$, TMS, 25° C.): δ0.85 (t, J=6.8 Hz, 6H), 1.20-1.29 (m, 28H), 1.32-1.38 (m, 4H), 1.45-1.50 (m, 8H), 1.54-1.59 (m, 4H), 2.02 (t, J=7.4 Hz, 4H), 2.09 (t, J=7.4 Hz, 4H), 2.99 (q, J=6.5 Hz, 4H), 4.08-4.47 (m, 2H), 7.73 (t, J=5.6 Hz, 2H), 7.97 (d, J=8.0 Hz, 2H).

Production of Compositions of Examples 1-14

Component (I) and component (II) described in the following Table 1 and Table 2 were mixed (numerical value of each component in the Tables is in wt %), stirred in LAB.MIXER (LM-110T, HANIL) for 1 min and dried at 50° C. for 8 hr to give the compositions of Examples 1-14.

Production of Compositions of Comparative Examples 1 and 2

Component (I) and component (II) described in the following Table 2 were mixed (numerical value of each component in the Tables is in wt %), stirred in LAB.MIXER (LM-110T, HANIL) for 1 min to give the compositions of Comparative Examples 1 and 2.

The compositions obtained by the above-mentioned production methods were evaluated for dispersibility, condition and durability of coated film, and sense of use (moist feeling, feeling of close adhesion, affinity). The evaluation methods and evaluation criteria are as follows.

Evaluation 1: Dispersibility (Oil Absorption)

As an index showing the dispersibility of a powder, oil absorption is generally used. For the evaluation of dispersibility, the oil absorption was measured as follows.

An oil agent (linseed oil) was added to samples (each 1 g) by small portions, and mixed with a spatula. The time point when the whole became one lump was taken as the end-point, the weight of the oil agent added before reaching the end-point was determined, and the oil absorption (%) was calculated from the following formula.

oil absorption (%)=weight (g) of oil agent÷weight (g) of sample×100

With the oil absorption of an untreated powder free of component (I) (hereinafter to be simply referred to as "untreated powder") as the standard, the difference from the oil absorption in the Examples and Comparative Examples was evaluated according to the following criteria.

⊙: decrease of not less than 5% in oil absorption was confirmed
○: decrease of not less than 2% and less than 5% in oil absorption was confirmed
Δ: decrease of less than 2% in oil absorption was confirmed
x: increase in oil absorption was confirmed Evaluation 2: Condition of Coated Film Samples (each 2 mg) were applied to artificial leather (Sapurare, manufactured by Idemitsu Technofine) with a force of 20-30 g to 1 cm square, and the appearance thereof was observed with a microscope (Video Loupe VL-7EX, manufactured by Scalar). On the basis of the obtained image, unevenness and sulcus cutis of the coated film were each scored according to the following criteria, and the sum was taken as the score of the coated film.

(Scoring Criteria of Evenness of Coated Film)
−1: coated film with unevenness
0: neither
+1: coated film without unevenness (Scoring Criteria of Noticeability of Sulcus Cutis)
−1: noticeable sulcus cutis
0: neither
+1: inconspicuous sulcus cutis Then, the difference from the scoring results of an untreated powder was evaluated according to the following criteria.

⊙: difference of not less than +2 points
○: difference of +1 points
Δ: difference of 0 point
x: difference of not more than −1 point Evaluation 3: Durability (Condition of Coated Film After Tape Detachment)

For the evaluation of durability of the coated film, the coated film after tape detachment was evaluated as follows. Cellophane tape (manufactured by NICHIBAN) was placed on the artificial leather after the above-mentioned evaluation 2 and closely adhered thereto by drawing a circle 5 times with the ball of a finger with a force of 50-70 g. The tape was peeled off, and the leather was observed again with a microscope (Video Loupe VL-7EX, manufactured by Scalar). On the basis of the obtained image, unevenness of coated film, sulcus cutis, and residual amount on crista cutis were scored according to the following criteria, and the sum was taken as the score of the coated film.

(Scoring Criteria of Evenness of Coated Film)
−1: coated film with unevenness
0: neither
+1: coated film without unevenness (Scoring Criteria of Noticeability of Sulcus Cutis)
−1: noticeable sulcus cutis
0: neither
+1: inconspicuous sulcus cutis Then, the difference from the scoring results of an untreated powder was evaluated according to the following criteria.

⊙: difference of not less than +2 points
○: difference of +1 points
Δ: difference of 0 point
x: difference of not more than −1 point Evaluations 4-6: Sense of Use As regards moist feeling, feeling of close adhesion, and affinity, the compositions (2 mg) prepared as mentioned above were applied to the skin within the range of 5×2 cm on the inner side of the forearm and tested in 8 healthy male and female test subjects. On the basis of the number of subjects who answered that the compositions of the Examples and Comparative Examples were superior as compared to an untreated powder, they were evaluated according to the following criteria. The test subjects were made to previously recognize the sense of use (moist feeling, feeling of close adhesion, affinity) of the untreated powder.

⊙: not less than 6 of test subjects acknowledge superiority
○: not less than 4 and less than 6 of test subjects acknowledge superiority
Δ: not less than 2 and less than 4 of test subjects acknowledge superiority
x: not more than 1 of test subjects acknowledges superiority The results are shown in Table 1 and Table 2.

TABLE 1

| | | | Example | | | | | |
|---|---|---|---|---|---|---|---|---|
| | | | 1 | 2 | 3 | 4 | 5 | 6 |
| I | component (A) | Production Example 1 as 10% aqueous solution | 5 | 20.0 | 40.0 | 100.0 | 150.0 | — |

TABLE 1-continued

|  |  |  | Example | | | | | |
|---|---|---|---|---|---|---|---|---|
|  |  |  | 1 | 2 | 3 | 4 | 5 | 6 |
|  |  | Production Example 2 as 10% aqueous solution | — | — | — | — | — | 50.0 |
| II | component (B) | silica | 99.5 | 98.0 | 96.0 | 90.0 | 85.0 | 95.0 |
| evaluation 1 |  | dispersibility (oil absorption) | ⊙ | ⊙ | ⊙ | ⊙ | ⊙ | ⊙ |
| evaluation 2 |  | condition of coated film | ○ | ⊙ | ⊙ | ⊙ | ⊙ | ⊙ |
| evaluation 3 |  | durability | ○ | ⊙ | ⊙ | ⊙ | ⊙ | ⊙ |
| evaluation 4 |  | moist feeling | ⊙ | ⊙ | ⊙ | ⊙ | ○ | ⊙ |
| evaluation 5 |  | feeling of close adhesion | ⊙ | ⊙ | ⊙ | ⊙ | ⊙ | ⊙ |
| evaluation 6 |  | affinity | ○ | ⊙ | ⊙ | ⊙ | ⊙ | ⊙ |

TABLE 2

|  |  |  | Example | | | | | | | | Comparative Example | |
|---|---|---|---|---|---|---|---|---|---|---|---|---|
|  |  |  | 7 | 8 | 9 | 10 | 11 | 12 | 13 | 14 | 1 | 2 |
| I | component (A) | Production Example 1 as 10% aqueous solution | 10.0 | 20.0 | 40.0 | 20.0 | 50.0 | — | 20.0 | — | — | — |
|  |  | Production Example 2 as 10% aqueous solution | — | — | — | — | — | 10.0 | — | 20.0 | — | — |
|  |  | N$^\varepsilon$-lauroyllysine | — | — | — | — | — | — | — | — | 5.0 | 1.0 |
| II | component (B) | titanium oxide | 99.0 | 98.0 | — | — | — | — | — | — | — | 99.0 |
|  |  | talc | — | — | 96.0 | — | 95.0 | — | — | — | 95.0 | — |
|  |  | mica | — | — | — | 98.0 | — | 99.0 | — | — | — | — |
|  |  | titanium oxide ultrafine particle (TTO-55(A)) | — | — | — | — | — | — | 98.0 | 98.0 | — | — |
| evaluation 1 |  | dispersibility (oil absorption) | ⊙ | ⊙ | ○ | ○ | ○ | ⊙ | ⊙ | ⊙ | Δ | Δ |
| evaluation 2 |  | condition of coated film | ⊙ | ⊙ | ○ | ○ | ○ | ⊙ | ○ | ⊙ | ⊙ | Δ |
| evaluation 3 |  | durability | ⊙ | ⊙ | ○ | ○ | ⊙ | ⊙ | ⊙ | ⊙ | Δ | Δ |
| evaluation 4 |  | moist feeling | ○ | ○ | ⊙ | ⊙ | ⊙ | ⊙ | ○ | ○ | X | X |
| evaluation 5 |  | feeling of close adhesion | ○ | ○ | ⊙ | ⊙ | ⊙ | ⊙ | ⊙ | ⊙ | X | X |
| evaluation 6 |  | affinity | ○ | ○ | ⊙ | ○ | ⊙ | ⊙ | ○ | ○ | X | X |

As is clear from Table 1 and Table 2, the compositions of the present invention (Examples 1-14) showed good dispersibility, and were superior in the condition and durability of coated film, and the sense of use such as moist feeling, feeling of close adhesion, and affinity.

Preferable blending examples of the composition of the present invention are explained below.

Blending Example 1 Pressed Powder Foundation

A pressed powder foundation of the formulation shown in the following Table 3 was prepared according to a conventional method.

TABLE 3

|  | wt % |
|---|---|
| talc, (dimethicone/methicone) copolymer | 18.40 |
| mica, (dimethicone/methicone) copolymer | 51.20 |
| titanium oxide, (dimethicone/methicone) copolymer | 8.00 |
| titanium oxide, aluminum stearate | 3.00 |
| zinc oxide, methicone | 2.00 |
| iron oxide (red), (dimethicone/methicone) copolymer | 0.40 |
| iron oxide (yellow), (dimethicone/methicone) copolymer | 1.00 |
| iron oxide (black), (dimethicone/methicone) copolymer | 0.15 |
| nylon-12 | 2.00 |
| compound of Production Example 1 (10%) | 2.00 |
| methylparaben | 0.05 |
| dimethicone | 5.78 |
| tetrapolyglyceryl isostearate-2 | 3.00 |
| phytosteryl/decyltetradecyl myristoyl methyl-β-alanine | 1.00 |
| mineral oil | 2.00 |
| methylparaben | 0.01 |
| tocopherol | 0.01 |
| total | 100.00 |

Blending Example 2 Stick Foundation

A stick foundation of the formulation shown in the following Table 4 was prepared according to a conventional method.

TABLE 4

| | wt % |
|---|---|
| octyldodecanol | 20.00 |
| dibutyllauroyl glutamide | 3.00 |
| dibutylethylhexanoyl glutamide | 2.00 |
| triethylhexanoin | 11.00 |
| ethylhexyl methoxycinnamate | 3.00 |
| hydrogenated polyisobutene | 20.00 |
| (hydroxystearic acid/stearic acid/rosin acid)dipentaerythrityl | 0.50 |
| tocopheryl acetate | 0.05 |
| butylparaben | 0.10 |
| propylparaben | 0.10 |
| (dimethicone/vinyldimethicone) crosspolymer | 2.00 |
| mica | 1.83 |
| titanium oxide, disodium stearoyl glutamate, myristic acid, aluminum hydroxide | 10.00 |
| titanium oxide treated with bis($N^\varepsilon$-lauroyl-L-lysine)sebacoyl amide disodium salt (Example 7) | 5.00 |
| cyclopentasiloxane | 11.00 |
| iron oxide (red), disodium stearoyl glutamate, aluminum hydroxide | 0.42 |
| iron oxide (yellow), disodium stearoyl glutamate, aluminum hydroxide | 1.41 |
| iron oxide (black), disodium stearoyl glutamate, aluminum hydroxide | 0.09 |
| quaternium-18 bentonite | 1.00 |
| boron nitride | 0.50 |
| silica | 7.00 |
| total | 100.00 |

Blending Example 3 Talc-Free Loose Powder Foundation

A talc-free loose powder foundation of the formulation shown in the following Table 5 was prepared according to a conventional method.

TABLE 5

| | wt % |
|---|---|
| mica | 56.30 |
| aluminum starch octenylsuccinate | 10.00 |
| titanium oxide, aluminum hydroxide | 15.00 |
| titanium oxide, aluminum stearate | 5.00 |
| iron oxide(red), aluminum stearate | 0.50 |
| iron oxide(yellow), aluminum stearate | 1.30 |
| iron oxide(black), aluminum stearate | 0.20 |
| treated silica treated with bis($N^\varepsilon$-lauroyl-L-lysine)sebacoyl amide disodium salt (Example 4) | 0.50 |
| lauroyllysine | 10.00 |
| methylparaben | 0.20 |
| grape seed oil | 0.59 |
| macadamia nut fatty acid phytosteryl | 0.20 |
| isopropyl lauroylsarcosine | 0.20 |
| tocopherol | 0.01 |
| total | 100.00 |

Blending Example 4 Sun Protector (O/W)

A Sun Protector (O/W) of the formulation shown in the following Table 6 was prepared according to a conventional method.

TABLE 6

| | wt % |
|---|---|
| sorbitan stearate | 0.90 |
| PEG-90 glyceryl isostearate | 2.60 |
| 1,2-pentanediol | 4.00 |
| behenyl alcohol | 1.00 |
| Polysorbate 80 | 1.50 |
| Steareth-2 | 0.50 |
| methylisothiazolinone | 0.05 |
| diethylamino hydroxybenzoyl hexyl benzoate, ethylhexyl methoxycinnamate | 10.00 |
| squalane | 3.00 |
| titanium oxide, isohexadecane, triethylhexanoin | 5.00 |
| titanium oxide ultrafine particles treated with bis($N^\varepsilon$-octanoyl-L-lysine)sebacoyl amide disodium salt (Example 14) | 3.00 |
| water | balance |
| alkyl acrylate copolymer | 2.50 |
| (ammonium acryloyldimethyltaurine/VP) copolymer, DPG, water | 22.50 |
| hydroxyethylurea, water | 2.00 |
| total | 100.00 |

Blending Example 5 Sunscreen (W/O)

A sunscreen (W/O) of the formulation shown in the following Table 7 was prepared according to a conventional method.

TABLE 7

| | wt % |
|---|---|
| stearic acid | 0.50 |
| cyclopentasiloxane, PEG-10 dimethicone, disteardimonium hectorite | 5.00 |
| dextrin palmitate | 0.30 |
| tocopheryl acetate | 0.05 |
| flavor: isopropyl myristate, hydroxycitronellal, hexyl cinnamal, benzyl salicylate, linalool | 0.30 |
| ethylhexyl methoxycinnamate | 6.00 |
| bis ethylhexyloxyphenol methoxyphenyl triazine | 2.00 |
| cyclopentasiloxane | 13.00 |
| (alkyl acrylate/dimethicone) copolymer, cyclopentasiloxane | 1.00 |
| zinc oxide, dimethicone, triethoxycaprylylsilane | 10.00 |
| titanium oxide, triethylhexanoin, isohexadecane, polyhydroxystearic acid, aluminum stearate, alumina | 10.00 |
| silica treated with bis($N^\varepsilon$-lauroyl-L-lysine)sebacoyl amide disodium salt (Example 3) | 4.00 |
| (vinyldimethicone/methicone sesquioxane) crosspolymer | 1.00 |
| polymethylsilsesquioxane | 1.00 |
| (styrene/acrylates) copolymer, water | 5.00 |
| iodopropynyl butylcarbamate | 0.30 |
| glycerol | 3.00 |

TABLE 7-continued

|  | wt % |
| --- | --- |
| dipropylene glycol | 3.00 |
| butylene glycol | 2.00 |
| magnesium sulfate | 0.70 |
| EDTA-2Na | 0.05 |
| water | balance |
| total | 100.00 |

Blending Example 6 Lipstick

A lipstick of the formulation shown in the following Table 8 was prepared according to a conventional method.

TABLE 8

|  | wt % |
| --- | --- |
| candelilla wax | 8.00 |
| paraffin | 6.00 |
| beeswax | 3.00 |
| carnauba wax | 2.00 |
| lanolin | 7.00 |
| castor oil | 16.00 |
| cetyl ethylhexanoate | 13.00 |
| ethylhexyl palmitate | 10.00 |
| hydrogenated polyisobutene | 5.00 |
| Red 202 | 1.05 |
| yellow 4 | 0.90 |
| Blue 1 | 0.04 |
| titanium oxide treated with bis($N^\varepsilon$-lauroyl-L-lysine)sebacoyl amide disodium salt (Example 7) | 1.60 |
| diisostearyl malate | 3.60 |
| methyl methacrylate crosspolymer | 0.50 |
| mica, titanium oxide | 1.00 |
| mica | 1.00 |
| phytosteryl/octyldodecyl lauroyl glutamate | 1.00 |
| bis-behenyl/isostearyl/phytosteryl dimer dilinoleyl dimer dilinoleate | 19.31 |
| total | 100.00 |

Blending Example 7 Stick Adiaphoretic

A stick adiaphoretic of the formulation shown in the following Table 9 was prepared according to a conventional method.

TABLE 9

|  | wt % |
| --- | --- |
| dibutyllauroyl glutamide | 3.0 |
| dibutylethylhexanoyl glutamide | 2.0 |
| hexyldecanol | 20.0 |
| cyclopentasiloxane | balance |
| isopropyl palmitate | 10.5 |
| aluminum chlorohydrate | 18.0 |
| talc | 6.0 |
| compound of Production Example 1 (10%) | 0.5 |
| tocopherol | q.s. |
| total | 100.0 |

The cosmetics of Blending Examples 1-7 all showed good dispersibility, were superior in the condition and durability of coated film, and superior in the sense of use such as moist feeling, feeling of close adhesion, and affinity.

The details of the materials used are as follows.
talc, (dimethicone/methicone) copolymer: talc DN-SH (manufactured by Dainihonkasei)
mica, (dimethicone/methicone) copolymer: SIO1-2 sericite FSE (manufactured by Dainihonkasei)
mica, (dimethicone/methicone) copolymer: mica MA-500 (manufactured by Dainihonkasei)
titanium oxide, (dimethicone/methicone) copolymer: titanium DN-SH(2) (manufactured by Dainihonkasei)
titanium oxide, aluminum stearate:MT-100Z (manufactured by TAYCA)
zinc oxide, methicone: MZ-303S (manufactured by TAYCA)
iron oxide (red), (dimethicone/methicone) copolymer: SIO1-2 Tarox R-516L (manufactured by Dainihonkasei)
iron oxide (yellow), (dimethicone/methicone) copolymer: SIO1-2 Tarox LLXLO (manufactured by Dainihonkasei)
iron oxide (black), (dimethicone/methicone) copolymer: SIO1-2 Tarox BL-100 (manufactured by Dainihonkasei)
nylon-12: ORGANOSOL 2002 NAT COS (manufactured by ARKEMA)
dimethicone: KF-96A-20cs (manufactured by Shin-Etsu Chemical Co., Ltd.)
tetrapolyglyceryl isostearate-2: COSMOL 44V (manufactured by Nisshin Oillio)
phytosteryl/decyltetradecyl myristoyl methyl-β-alanine: ELDEW APS-307 (manufactured by Ajinomoto Co., Inc.)
mineral oil: Moresco white P-70 (manufactured by Matsumura Sekiyu Co., Ltd.)
octyldodecanol: Risonol 20SP (manufactured by Kokyu Alcohol Kogyo Co., Ltd.)
dibutyllauroyl glutamide: oil gelling agent based on amino acid GP-1 (manufactured by Ajinomoto Co., Inc.)
dibutylethylhexanoyl glutamide: oil gelling agent based on amino acid EB-21 (manufactured by Ajinomoto Co., Inc.)
triethylhexanoin: TOG (manufactured by Kokyu Alcohol Kogyo Co., Ltd.)
ethylhexyl methoxycinnamate: PARSOL MCX (manufactured by DSM NUTRITIONAL PRODUCTS LTD.)
hydrogenated polyisobutene: Parleam 18 (manufactured by NOF)
(hydroxystearic acid/stearic acid/rosin acid) dipentaerythrityl: COSMOL 168ARV (manufactured by Nisshin Oillio)
(dimethicone/vinyldimethicone)crosspolymer: Trefil E-506S (manufactured by Dow Corning Toray Co., Ltd Corporation)
mica: micaY-2300 (manufactured by Yamaguchi Mica)
titanium oxide, disodium stearoyl glutamate, myristic acid, aluminum hydroxide: NAI-titanium CR-50 (manufactured by Miyoshi Kasei)
cyclopentasiloxane: SH245 Fluid (manufactured by Dow Corning Toray Co., Ltd Corporation)
iron oxide (red), disodium stearoyl glutamate, aluminum hydroxide: NAI-red R-516PS (manufactured by Miyoshi Kasei)
iron oxide (yellow), disodium stearoyl glutamate, aluminum hydroxide: NAI-yellow LL-100PS (manufactured by Miyoshi Kasei)
iron oxide(black), disodium stearoyl glutamate, aluminum hydroxide: NAI-black BL-100PS (manufactured by Miyoshi Kasei)
quaternium-18 bentonite: S-BEN W (manufactured by HOJUN Co., Ltd.)
boron nitride: BN leaf powder SHP-3 (manufactured by MIZUSHIMA FERROALLOY CO., LTD.)
silica: silicamicrobeet P-1500, L-1500 mixed at 2:5 (all manufactured by JGC Catalysts and Chemicals Ltd)
octenylsuccinic acid starch Al: Dry-Flo PC (manufactured by AKZO NOBEL) titanium oxide, Aluminum hydroxide: CR-50 (manufactured by Ishihara Sangyo Kaisha, LTD.)

titanium oxide, Aluminum stearate: MST-1 TiO$_2$ R250 (manufactured by DAITO KASEI KOGYO CO., LTD.)
iron oxide (red), Aluminum stearate: MST-1 RED No. 211P (manufactured by DAITO KASEI KOGYO CO., LTD.)
iron oxide (yellow), Aluminum stearate: MST-1 YELLOW No. 602P (manufactured by DAITO KASEI KOGYO CO., LTD.)
iron oxide(black), Aluminum stearate: MST-1 BLACK No. 710P (manufactured by DAITO KASEI KOGYO CO., LTD.)
lauroyllysine: AMIHOPE LL (manufactured by Ajinomoto Co., Inc.)
grapes seed oil: NIKKOL grape seed oil (manufactured by Nikko Chemicals)
macadamia nut fatty acid phytosteryl: YOFCO MAS(Nippon Fine Chemical manufactured by)
isopropyl lauroylsarcosine: ELDEW SL-205 (manufactured by Ajinomoto Co., Inc.)
sorbitan stearate: EMALEX SPE-100S (manufactured by Nihon Emulsion Co., Ltd.)
PEG-90 glyceryl isostearate: EMALEX GWIS-150EX (manufactured by Nihon Emulsion Co., Ltd.)
1,2-pentanediol: Hydrolite-5 (manufactured by Symrise)
Polysorbate 80: Rheodol TW-O120V (manufactured by Kao Corporation)
Steareth-2: EMALEX 602 (manufactured by Nihon Emulsion Co., Ltd.)
methylisothiazolinone: Zonen MT-10 (manufactured by CHEMICREA Inc.)
diethylamino hydroxybenzoyl hexyl benzoate, ethylhexyl methoxycinnamate: UVINUL A Plus B (manufactured by BASF)
titanium oxide, isohexadecane, triethylhexanoin: UVINUL A Plus B (manufactured by BASF)
squalane: squalane (manufactured by Maruha Nichiro Corporation)
alkyl acrylate copolymer: Dermacryl AQ-F (manufactured by AKZO NOBEL)
(ammonium acryloyldimethyltaurine/VP) copolymer, DPG, water: Aristoflex AVS (manufactured by Clariant)
hydroxyethylurea, water: Hydrovance (manufactured by AKZO NOBEL)
stearic acid: NAA-180 (manufactured by NOF)
cyclopentasiloxane, PEG-10 dimethicone, disteardimonium hectorite: NIKKOL Nikkomulese W (manufactured by Nikko Chemicals)
dextrin palmitate: Rheopearl TL2 (manufactured by Chiba Flour Milling Co., Ltd.)
bis ethylhexyloxyphenol methoxyphenyl triazine: Tinosorb S (manufactured by BASF)
(alkyl acrylate/dimethicone) copolymer, cyclopentasiloxane: KP-545 (manufactured by Shin-Etsu Chemical Co., Ltd.)
zinc oxide, dimethicone, triethoxycaprylylsilane: ALISZ-031 (manufactured by Miyoshi Kasei Industry Co., Ltd.)
titanium oxide, triethylhexanoin, isohexadecane, polyhydroxystearic acid, aluminum stearate, alumina: Solaveil CT-434 (manufactured by Croda)
(vinyldimethicone/methicone sesqui oxane) crosspolymer: KSP-102 (manufactured by Shin-Etsu Chemical Co., Ltd.)
polymethylsilsesquioxane: KMP-590 (manufactured by Shin-Etsu Chemical Co., Ltd.)
(styrene/acrylates) copolymer, water: ROHMSPHERE GEL (manufactured by DOW)
iodopropynyl butylcarbamate: Glycasil 2000 (manufactured by Lonza)
glycerol: concentrate glycerol for cosmetics (manufactured by Sakamoto Yakuhin Kogyo Co., Ltd.)
dipropyleneglycol: DPG-RF (manufactured by ADEKA)
butyleneglycol: 1,3-B.G. (manufactured by Daicel Corporation)
EDTA-2Na: Dissolvine NA (manufactured by AKZO NOBEL)
candelilla wax: Candelilla NC-1630 (manufactured by CERARICA NODA Co., Ltd.)
paraffin: paraffin wax 155 (manufactured by Nippon Seiro)
beeswax: WHITE BEES WAX (manufactured by Miki Chemical Industry)
Carnauba wax: Carnauba wax No. 1 (manufactured by CERARICA NODA Co., Ltd.)
lanolin: the Japanese Pharmacopoeia purification lanolin (manufactured by CERARICA NODA Co., Ltd.)
castor oil: purified castor oil (manufactured by NIKKA OIL MILLS CO., LTD)
cetyl ethylhexanoate: EXCEPARL (manufactured by Kao Corporation)
ethylhexyl palmitate: salacos P-O (manufactured by. Nisshin Oillio)
hydrogenated polyisobutene: Parleam 18 (manufactured by NOF)
red 202: red No. 202 (manufactured by Taketombo Co., LTD.)
yellow 4: red No. 4 aluminum lake (manufactured by Taketombo Co., LTD.)
blue1: blue No. 1 aluminum lake (manufactured by Taketombo Co., LTD.)
diisostearyl malate: COSMOL 222 (manufactured by Nisshin Oillio)
methyl methacrylate crosspolymer: Matsumoto microsphere MHB-R (manufactured by Matsumoto Yushi-Seiyaku Co., Ltd)
mica, titanium oxide: FlamencoPearl 110C (manufactured by BASF)
mica: PROMINENCE SF (manufactured by NIHON KOKEN KOGYO CO., LTD.)
phytosteryl/octyldodecyl lauroyl glutamate: ELDEW PS-203R (manufactured by Ajinomoto Co., Inc.)
bis-behenyl/isostearyl/phytosteryl dimer dilinoleyl dimer dilinoleate: Plandool G (manufactured by Nippon Fine Chemical)
hexyldecanol: Risonol 16SP (manufactured by Kokyu Alcohol Kogyo Co., Ltd.)
isopropyl palmitate: IPP (manufactured by Kokyu Alcohol Kogyo Co., Ltd.)
aluminum chlorohydrate: CHLORHYDROL Powder (manufactured by REHEIS)

INDUSTRIAL APPLICABILITY

The present invention can provide a composition which can be produced conveniently, shows good dispersibility, and is superior in the sense of use such as moist feeling, feeling of close adhesion, and affinity. Since a coated film formed from the composition has good condition and is superior in durability, it can be widely utilized as cosmetics.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A dry surface-treated powder, comprising:
   (A) at least one compound selected from the group consisting bis($N^\varepsilon$- lauroyl-L-lysine)sebacoyl amide, a salt of bis($N^\varepsilon$-lauroyl-L-lysine)sebacoyl amide, bis($N^\varepsilon$-octanoyl-L-lysine)sebacoyl amide, and a salt of bis($N^\varepsilon$-octanoyl-L-lysine)sebacoyl amide;
   coated on
   (B) at least one kind of inorganic powder selected from the group consisting of talc, mica, sericite, iron oxide, titanium oxide, zinc oxide, and aluminum hydroxide,
   wherein said (A) and said (B) are present in a weight ratio, weight of (A)/weight of (B), in a range of 1/200 to 1/5.

2. A cosmetic, comprising a composition according to claim 1.

3. The composition according to claim 1, wherein said (A) is at least one compound selected from the group consisting a sodium salt of bis($N^\varepsilon$-lauroyl-L-lysine)sebacoyl amide and a sodium salt of bis($N^\varepsilon$-octanoyl-L-lysine)sebacoyl amide.

4. A cosmetic, comprising a composition according to claim 3.

5. A method of producing a surface-treated powder, comprising:
   coating a surface of
   (B) at least one kind of inorganic powder selected from the group consisting of talc, mica, sericite, iron oxide, titanium oxide, zinc oxide, and aluminum hydroxide, with
   (A) at least one compound selected from the group consisting bis($N^\varepsilon$-lauroyl-L-lysine)sebacoyl amide, a salt of bis($N^\varepsilon$-lauroyl-L-lysine)sebacoyl amide, bis($N^\varepsilon$-octanoyl-L-lysine)sebacoyl amide, and a salt of bis($N^\varepsilon$-octanoyl-L-lysine)sebacoyl amide,
   drying the coated at least one kind of inorganic powder,
   wherein, during said coating, said (A) and said (B) are present in a weight ratio, weight of (A)/weight of (B), in a range of 1/200 to 1/5.

* * * * *